US009125605B2

(12) United States Patent
Tone et al.

(10) Patent No.: US 9,125,605 B2
(45) Date of Patent: Sep. 8, 2015

(54) BIOLOGICAL SIGNAL MEASURING APPARATUS

(75) Inventors: Katsuhide Tone, Tokyo (JP); Katsuyoshi Suzuki, Tokyo (JP)

(73) Assignee: Nihon Kohden Corporation, Tokyo (JP)

( * ) Notice: Subject to any disclaimer, the term of this patent is extended or adjusted under 35 U.S.C. 154(b) by 275 days.

(21) Appl. No.: 13/606,265

(22) Filed: Sep. 7, 2012

(65) Prior Publication Data
US 2013/0066177 A1 Mar. 14, 2013

(30) Foreign Application Priority Data

Sep. 13, 2011 (JP) ................................ 2011-199269

(51) Int. Cl.
*A61B 5/1455* (2006.01)
*A61B 5/00* (2006.01)

(52) U.S. Cl.
CPC ........... *A61B 5/14551* (2013.01); *A61B 5/7203* (2013.01); *A61B 5/7257* (2013.01); *A61B 2560/0209* (2013.01)

(58) Field of Classification Search
CPC ............... A61B 5/7203; A61B 5/7257; A61B 5/14551; A61B 2560/0209
USPC .......................... 600/310, 322, 323, 330, 336
See application file for complete search history.

(56) References Cited

U.S. PATENT DOCUMENTS

| | | | |
|---|---|---|---|
| 5,431,170 A * | 7/1995 | Mathews | 600/323 |
| 5,853,364 A | 12/1998 | Baker, Jr. et al. | |
| 6,022,321 A | 2/2000 | Amano et al. | |
| 6,155,983 A | 12/2000 | Kosuda et al. | |
| 6,217,523 B1 | 4/2001 | Amano et al. | |
| 6,361,501 B1 | 3/2002 | Amano et al. | |
| 6,434,408 B1 * | 8/2002 | Heckel | 600/336 |
| 7,215,984 B2 * | 5/2007 | Diab et al. | 600/323 |
| 2003/0028085 A1 | 2/2003 | Al-Ali | |

(Continued)

FOREIGN PATENT DOCUMENTS

| | | |
|---|---|---|
| JP | 788092 A | 4/1995 |
| JP | 10-258038 A | 9/1998 |

(Continued)

OTHER PUBLICATIONS

Extended European Search Report, dated Nov. 29, 2012, issued by the European Patent Office in counterpart European Patent Application No. 12183165.5.

(Continued)

*Primary Examiner* — Eric Winakur
(74) *Attorney, Agent, or Firm* — Sughrue Mion, PLLC

(57) ABSTRACT

The calculation amount of the whole can be reduced. A biological signal measuring apparatus includes a biological signal measuring unit which measures a biological signal; and a calculation processing unit which performs calculation processes on the measured biological signal, wherein the calculation processing unit has: a first calculation processing unit which performs calculation processes required for calculating the biological signal, and which is independently controllable; and a second calculation processing unit which performs a specific calculation process, and which is independently controllable, and, when the first calculation processing unit satisfies given conditions, the second calculation processing unit is caused to perform the specific calculation process.

16 Claims, 3 Drawing Sheets

(56) References Cited

U.S. PATENT DOCUMENTS

| | | |
|---|---|---|
| 2003/0120160 A1 | 6/2003 | Yarita |
| 2004/0092805 A1 | 5/2004 | Yarita |
| 2005/0187446 A1 | 8/2005 | Nordstrom et al. |
| 2006/0122476 A1 | 6/2006 | Van Slyke |
| 2006/0287587 A1 | 12/2006 | Yarita |
| 2006/0287588 A1 | 12/2006 | Yarita |
| 2010/0125188 A1 | 5/2010 | Schilling et al. |

FOREIGN PATENT DOCUMENTS

| | | |
|---|---|---|
| JP | 11-113862 A | 4/1999 |
| JP | 2003-235819 A | 8/2003 |
| JP | 4196209 B2 | 10/2008 |
| JP | 4352315 B2 | 8/2009 |
| JP | 2010233908 A | 10/2010 |
| WO | 9215955 A1 | 9/1992 |
| WO | 2010/113649 A1 | 10/2010 |

OTHER PUBLICATIONS

Office Action issued Aug. 21, 2014 by the Japanese Patent Office in corresponding Japanese Application No. 2011-199269.

Office Action dated Mar. 31, 2015 issued by Japanese Patent Office in counterpart Japanese Patent Application No. 2011-199269.

* cited by examiner

BIOLOGICAL SIGNAL MEASURING APPARATUS

BACKGROUND OF THE INVENTION

The present invention relates to a biological signal measuring apparatus in which, while maintaining performance such as a noise processing function, the power consumption can be reduced and a long-term continuous use is enabled.

As one example of a biological signal measuring apparatus, a pulse oximeter which non-invasively measures the oxygen saturation of arterial blood is widely used (for example, see Patent Reference 1). In a measurement of the oxygen saturation by a conventional pulse oximeter, a probe is first attached to the tip of a finger or ear lobe of the subject, and the attached portion of the subject is illuminated in a time sharing manner with light beams of two different wavelengths or a red light beam and infrared light beams emitted from the probe. In the illuminating light beams, the transmitted light beam which is transmitted through the tissue of the finger tip or the ear lobe, or the reflected light beam which is reflected by the inside and outside of the tissue is detected for each of the wavelengths. The oxygen saturation is calculated from a ratio of pulsation components of absorbances obtained from the result of the detection.

PRIOR ART REFERENCE

Patent Reference (Patent Reference 1) JP-A-2010-233908
(Patent Reference 2) Japanese Patent No. 4,196,209
(Patent Reference 3) Japanese Patent No. 4,352,315
(Patent Reference 4) WO92/015955
(Patent Reference 5) JP-A-7-88092
(Patent Reference 6) U.S. Pat. No. 5,853,364

In the conventional pulse oximeter, all of the calculation processes in the case where the oxygen saturation is calculated from the result of the detections of the light beams of the wavelengths are performed by an incorporated CPU (Central Processing Unit). In a pulse oximeter having a function of eliminating body motion noise configured by various kinds of noises which are caused, for example, by body motions (see, for example, Patent References 2 and 3), a CPU performs not only the calculation of the oxygen saturation, but also filtering of motion noise, and therefore the processing load on the CPU is large. For example, there is a case where the processing time which is required for a CPU to eliminate motion noise occupies about ¾ of all the time which is required for the CPU to perform all of the calculation processes. In a pulse oximeter having such a function of eliminating body motion noise, therefore, a high-performance CPU must be mounted in order to perform noise elimination while satisfying the cycle time. The increase of the calculation amount due to noise elimination leads directly to that of the power consumption. The power consumption of a CPU accounts for about 60% of that of a pulse oximeter. In a portable pulse oximeter which is driven by electric power supplied from batteries, therefore, there is a problem in that the life of the batteries is shortened.

In addition, a wide variety of other methods of eliminating body motion noise have been known (for example, see Patent References 4 to 6).

SUMMARY

This invention provides a biological signal measuring apparatus including: a biological signal measuring unit which measures a biological signal; and a calculation processing unit which performs calculation processes on the measured biological signal, wherein the calculation processing unit has: a first calculation processing unit which performs calculation processes required for calculating the biological signal; and a second calculation processing unit which performs a specific calculation process, the first calculation processing unit and the second calculation processing unit are independently controllable with each other, and, when the first calculation processing unit satisfies given conditions, the second calculation processing unit is caused to perform the specific calculation process.

The second calculation processing unit may perform the specific calculation process with a smaller calculation amount as compared with a case of the first calculation processing unit.

The specific calculation process may be at least one of a simple process, a routine process, and a parallel process.

The specific calculation process may be a calculation process specialized for elimination of body motion noise and extraneous light noise which are contained in the measured biological signal.

The given conditions may include at least one of reduction of a quality of the measured biological signal, detection of a body motion, and detection of extraneous light.

In the second calculation processing unit, a unit data length for the calculation process may be variable in accordance with a kind of the calculation process, and shorter than a unit data length for the calculation processes performed by the first calculation processing unit.

The first calculation processing unit may determine whether the first calculation processing unit causes the second calculation processing unit to perform the calculation process or not, based on predetermined conditions, and, only when the first calculation processing unit determines to cause the second calculation processing unit to perform the calculation process, may supply data to the second calculation processing unit.

In a case where a load of the calculation process due to a noise component exceeds a predetermined level, the first calculation processing unit may supply data to the second calculation processing unit.

The calculation processing unit may further have a disturbance detecting unit which can detect a disturbance cause that generates noises in a result of the measurement of the biological signal, and, in a case where the disturbance detecting unit detects the disturbance cause, the first calculation processing unit may cause the second calculation processing unit to perform the specific calculation process.

The disturbance detecting unit may include at least one of an acceleration sensor which detects a body motion, and an optical sensor which detects extraneous light.

The calculation processing unit may further have a determining unit that determines which one of a first calculation result obtained by the first calculation processing unit and a second calculation result obtained by the second calculation processing unit is optimum, and may output a calculation result which is determined to be optimum by the determining unit.

The biological signal measuring unit may include: a light emitter which illuminates living tissue containing arterial blood flow, with light beams of two different wavelengths or a red light beam and an infrared light beam at different timings; and a light receiver which receives the light beams that are emitted from the light emitter and transmitted through or reflected from the living tissue, and which converts the light beams to an electric signal corresponding to the receiving intensities of the light beams of the respective wavelengths, and the first calculation processing unit may calculate a ratio of pulsation components of an absorbance due to the arterial blood flow with respect to the light beams of two wavelengths, from data which are produced based on the electric signal, and may calculate an oxygen saturation of arterial blood based on the ratio of pulsation components.

DETAILED DESCRIPTION OF EMBODIMENTS

Hereinafter, the invention will be described through a preferred embodiment of the invention. The following embodiment is not intended to limit the features of the invention defined in the appended claims. Moreover, all combinations of configurations in the following description of the embodiment are not necessarily essential in embodying the invention.

Figure 1:
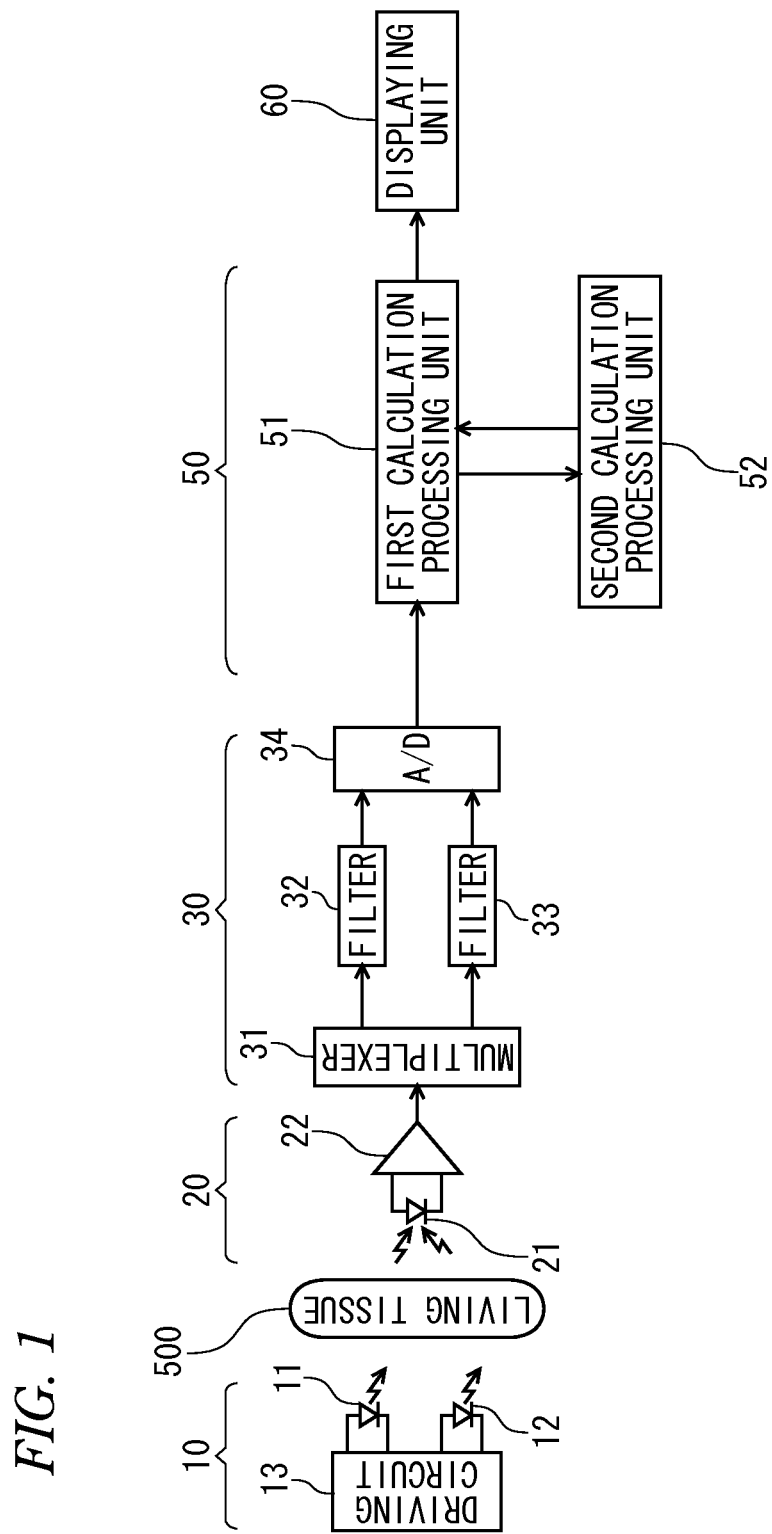
FIG. 1 is a view showing the functional configuration of a pulse oximeter 1 of an embodiment of the invention.

FIG. 1 is a view showing the functional configuration of a pulse oximeter 1 of an embodiment of the invention. As shown in FIG. 1, the pulse oximeter 1 is an apparatus which measures the oxygen saturation of arterial blood of the subject, and includes a light emitter 10, a light receiver 20, an extracting unit 30, a calculation processing unit 50, and a displaying unit 60. The pulse oximeter 1 is an example of the biological signal measuring apparatus of the invention, and the light emitter 10 and the light receiver 20 constitute a biological signal measuring unit.

The light emitter 10 has light emitting elements 11, 12 and a driving circuit 13. The light emitting elements 11, 12 are driven by the driving circuit 13 so as to alternately emit two light beams of different wavelengths. In the example, the light emitting element 11 is a light emitting diode which emits an infrared light beam (IR) of a wavelength of about 940 nm, and the light emitting element 12 is a light emitting diode which emits a red light beam (R) of a wavelength of about 660 nm.

The light receiver 20 has a light receiving element 21 and an amplifier 22. When the light beams of the two different wavelengths are alternately emitted from the light emitter 10 toward the living tissue 500 of the subject, the light receiving element 21 receives the light beams of the respective wavelengths which are transmitted through or reflected from the living tissue 500, and converts the light beams to an electric signal corresponding to the receiving intensities of the light beams. The amplifier 22 amplifies the electric signal supplied from the light receiving element 21, by a given amplification factor. In the example, the light receiving element 21 is a photodiode, and the living tissue 500 is, for example, the tip of a finger or ear lobe of the subject.

The extracting unit 30 has a multiplexer 31, a filter 32, a filter 33, and an A/D converter 34. The multiplexer 31 splits the electric signal which is amplified in the amplifier 22, into electric signals respectively corresponding to the light wavelengths (R and IR). The electric signals which are obtained by the split in the multiplexer 31, and which correspond to R and IR, respectively are input into the filters 32, 33, respectively. The filters 32, 33 filter out variation components and the like caused by the respiration of the subject from the input electric signals, and allow components other than the variation components to pass therethrough. The A/D converter 34 digitizes the electric signals which are filtered in the filters 32, 33, respectively.

In the case where the respiratory rate of the subject is unknown, a frequency analyzing unit which can perform a fast Fourier transform on an incoming electric signal may be disposed in the front stage of each of the filters 32, 33, so that the frequencies of the electric signals respectively corresponding to R and IR are analyzed and the frequency components corresponding to the respiratory rate of the subject are specified. In this case, preferably, the filters 32, 33 are variable bandpass filters in which the frequency components to be extracted can be changed following the variations in the respiratory rate measured by the respective frequency analyzing portions in the front stages. Alternatively, the filters 32, 33 may not be disposed, and the filtering process may be performed by the calculation processing unit 50.

The calculation processing unit 50 has a first calculation processing unit 51 and a second calculation processing unit 52. In the example, the A/D converter 34 and the first calculation processing unit 51, and the first calculation processing unit 51 and the second calculation processing unit 52 are connected to each other by, for example, an 8-bit data bus. Preferably, the first calculation processing unit 51 and the second calculation processing unit 52 are configured by respective elements which are independently controllable, and which are physically different from each other.

In the example, the first calculation processing unit 51 is a CPU (Central Processing Unit), and calculates the oxygen saturation of arterial blood from the digitized electric signals respectively corresponding to the light beams of the two wavelengths. More specifically, the first calculation processing unit 51 calculates a ratio $\Phi 1$ of the absorbances of the two calculated wavelengths which is given by $\Phi 1 = \Delta A_R / \Delta A_{IR}$ where $\Delta A_R$ is the pulsation component of the absorbance of the wavelength of the red light beam (R), and $\Delta A_{IR}$ is the pulsation component of the absorbance of the wavelength of the infrared light beam (IR), based on the Lambert-Beer Law. Then, the first calculation processing unit 51 calculates the oxygen saturation of arterial blood, pulse rate of the subject, and the like, based on the calculated ratio $\Phi 1$ of the absorbances of the two wavelengths, and outputs the result of the calculation to the displaying unit 60 while associating the result with timing data. The displaying unit 60 displays the current value of the oxygen saturation of arterial blood, the temporal change of the value, and the like which are supplied from the first calculation processing unit 51.

When given conditions are satisfied, the first calculation processing unit 51 causes the second calculation processing unit 52 which will be described later, to execute a specific calculation process, and performs an output operation with using a result of the calculation. Specific examples of the given conditions are that the qualities of the digitized electric signals respectively corresponding to the two wavelengths are lowered (for example, the S/N ratio is reduced), and that the noise component caused by body motions, extraneous light such as fluorescent light is mixed. However, the conditions are not limited to the examples.

In the calculation of the oxygen saturation, the first calculation processing unit 51 may perform a fast Fourier transform (FFT) on the ratio $\Phi 1$ of the absorbances of the two wavelengths. In the case where a frequency component is detected which is largely different from a frequency component (pulsation component) that is detected during the steady state, the first calculation processing unit 51 determines that the ratio $\Phi 1$ of the absorbances of the two wavelengths contains an unsteady frequency component such as body motion noise. Moreover, the first calculation processing unit 51 outputs information related to the pulsation component to the second calculation processing unit 52.

In the example, the second calculation processing unit 52 is an FPGA (Field Programmable Gate Array), and has logic circuits which are specialized respectively for processes of eliminating body motion noise and extraneous light noise (more specifically, specific processes used in the elimination of body motion noise and extraneous light noise, such as a simple process, a routine process, and a parallel process). In the example, in the case where the first calculation processing unit 51 satisfies the given conditions, the second calculation processing unit 52 receives the digitized electric signals respectively corresponding to the light beams of the two wavelengths through the first calculation processing unit 51, and executes the specific calculation processes.

Then, the second calculation processing unit 52 sequentially performs in a given cycle time processes of calculating the oxygen saturation of arterial blood, including processes (in the embodiment, processes particularly related to elimination of body motion noise) of a fast Fourier transform (FFT), a signal/noise waveform separation (sum of products calculation), a discrete Fourier transform (DFT), and a filter process (sum of products calculation). The processing unit calculates an absorbance $\Phi 2$ from which an unsteady frequency component such as body motion noise is eliminated, from the input electric signals of the two wavelengths, and outputs the result of the calculation to the first calculation processing unit 51 while associating the result with timing data.

In the second calculation processing unit 52, the unit data lengths in the calculation processes are variable, and the unit data lengths in the logic circuits may be different from each other. In the example, particularly, the length of data processed in the second calculation processing unit 52 is shorter than that of data processed in the first calculation processing unit 51. More specifically, in the first calculation processing unit 51, all kinds of calculation processes are performed with the same unit data length, and therefore the unit data length of, for example, 32 bits must be ensured. In the first calculation processing unit 51, depending on the kind of process, therefore, a calculation process is performed even on redundant data in which a significant portion of the unit data length does not affect the process result.

In the second calculation processing unit 52, by contrast, the minimum data length (8 to 26 bits) which is required for performing the corresponding calculation process can be adequately set as the unit data length for each of the three kinds of logic circuits. Preferably, a part of the second calculation processing unit 52 may be set as a memory of arbitrary size. Therefore, the second calculation processing unit 52 can perform the calculation process with a smaller calculation amount as compared with the first calculation processing unit 51. When the second calculation processing unit 52 performs calculation processes related to the elimination of body motion noise, the calculation amount of the whole is reduced, and hence the time elapsed until obtaining a process result is shortened as compared with the case where the first calculation processing unit 51 performs the calculation processes. When compared to the case where processes extending to the calculation processes related to the elimination of body motion noise are performed only by the first calculation processing unit 51, therefore, a CPU which operates at a lower clock frequency, and which includes a lower-capacity RAM can be used in the first calculation processing unit 51, so that it is possible to expand the range of choices for components applicable to the first calculation processing unit 51. Since the whole calculation amount is reduced, also the power consumption can be reduced. In the case where the pulse oximeter 1 is driven by batteries, therefore, the driving time of the pulse oximeter 1 can be prolonged. In the case where the kinds of circuits to be disposed in the second calculation processing unit 52 are specified, the utilization rate of an FPGA to be used in the second calculation processing unit 52 can be enhanced, and therefore the mounting area can be further reduced.

In experiments conducted by the applicant, measurements of the oxygen saturation including processes for body motion noise and extraneous light noise were performed in the same cycle time by using each of a pulse oximeter (pulse oximeter A) including only a CPU and a pulse oximeter (pulse oximeter B) including both a CPU and an FPGA. As a result, even when a CPU in which the operation speed is ¼ of that of the CPU of the pulse oximeter A was used in the pulse oximeter B, the processing speed of the pulse oximeter B was not different from that of the pulse oximeter A, and the power consumption of the calculation processing unit in the pulse oximeter B was about half of that in the pulse oximeter A.

In the example, the first calculation processing unit 51 may be configured so as to have a function of a determining unit that receives the result of the calculation process performed by the second calculation processing unit 52, and that determines based on predetermined conditions which one of the result and that of the calculation process performed by itself is optimum as an output waveform. More specifically, in the example, if, based on the result of the fast Fourier transform (FFT) on the ratio $\Phi 1$ of the absorbances of the two wavelengths, the first calculation processing unit 51 determines that the ratio $\Phi 1$ does not contain an unsteady frequency component such as body motion noise, the processing unit outputs the result of the calculation process performed by itself to the displaying unit 60, and, if the processing unit determines that the ratio $\Phi 1$ contains body motion noise, outputs the result of the calculation process performed by the second calculation processing unit 52 to the displaying unit 60.

As described above, in accordance with whether $\Phi 1$ contains a noise component such as body motion noise or not, the first calculation processing unit 51 outputs to the displaying unit 60 the result of the process from which the noise component is eliminated, and which is obtained by the second calculation processing unit 52, or the result of the process in which the elimination of noise component is not performed, which is more similar to the input signal, and which is obtained by the first calculation processing unit 51. Therefore, the waveform in which the influence of body motion is eliminated is displayed on the displaying unit 60 irrespective of existence of body motion or extraneous light.

Figure 2:
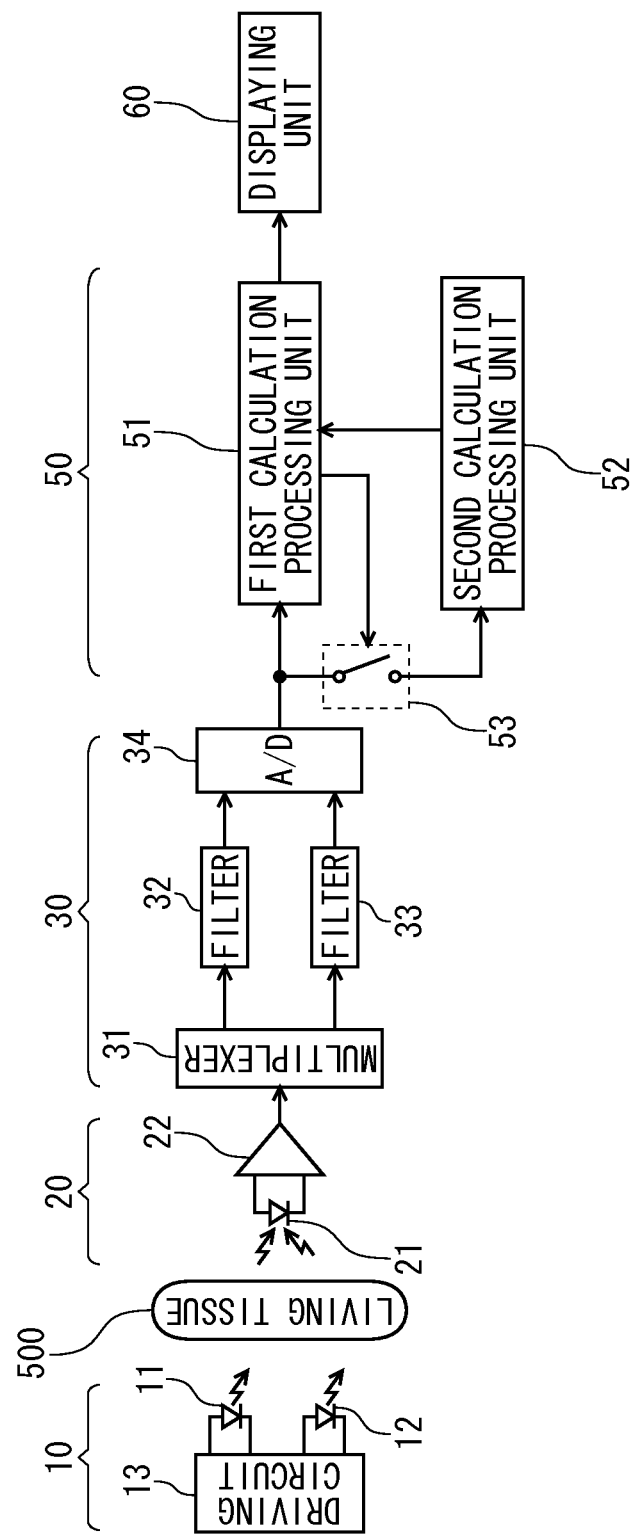
FIG. 2 is a view showing the functional configuration of a pulse oximeter 2 of another example of the embodiment of the invention.

FIG. 2 is a view showing the functional configuration of a pulse oximeter 2 of another example of the embodiment of the invention. Description about the components of the pulse oximeter 2 of the example which are similar to those of the pulse oximeter 1 that has been described with reference to FIG. 1 is omitted.

As shown in FIG. 2, the calculation processing unit 50 of the pulse oximeter 2 of the example includes the first calculation processing unit 51, the second calculation processing unit 52, and a switch 53. In the example, the A/D converter 34 is connected to the first calculation processing unit 51 by the data bus, and also to the second calculation processing unit 52 by another data bus through the switch 53. In the example, in a state where a driving signal which is described later is not given from the first calculation processing unit 51 to the switch 53, the switch is in an OFF state (where the bus line between the A/D converter 34 and the second calculation processing unit 52 is interrupted).

In the pulse oximeter 2 of the example, only when, based on the result of the fast Fourier transform on the ratio Φ1, or the like, the first calculation processing unit 51 determines that the ratio Φ1 contains an unsteady frequency component such as body motion noise, the switch 53 is turned ON. Only when the first calculation processing unit 51 determines that the input signal contains a noise component such as body motion noise, therefore, the second calculation processing unit 52 receives data from the A/D converter 34 and performs a calculation process. In this case, the second calculation processing unit 52 may output a result of the calculation process to the first calculation processing unit 51 in a similar manner as the pulse oximeter 1, but alternatively may directly output the process result to the displaying unit 60.

In the pulse oximeter 2 of the example, as described above, the second calculation processing unit 52 is activated only when required, and hence the power consumption of the whole can be reduced. The trigger for causing the second calculation processing unit 52 to perform the process is not limited to the above, and may be realized by any means as far as it can determine the occurrence of a body motion. In the case where, when the process of calculating the oxygen saturation of arterial blood and the pulse rate from the ratio Φ of the absorbances of the two wavelengths is being performed, the load of the calculation process due to the noise component exceeds a predetermined level, the first calculation processing unit 51 may turn ON the switch 53 so that the second calculation processing unit 52 performs the process of calculating the ratio Φ2 of the absorbances. Anyhow, the first calculation processing unit 51 preferably calculates the oxygen saturation, the pulse rate, and the like based on either of the absorbance ratios Φ1 and Φ2 which is optimum.

Figure 3:
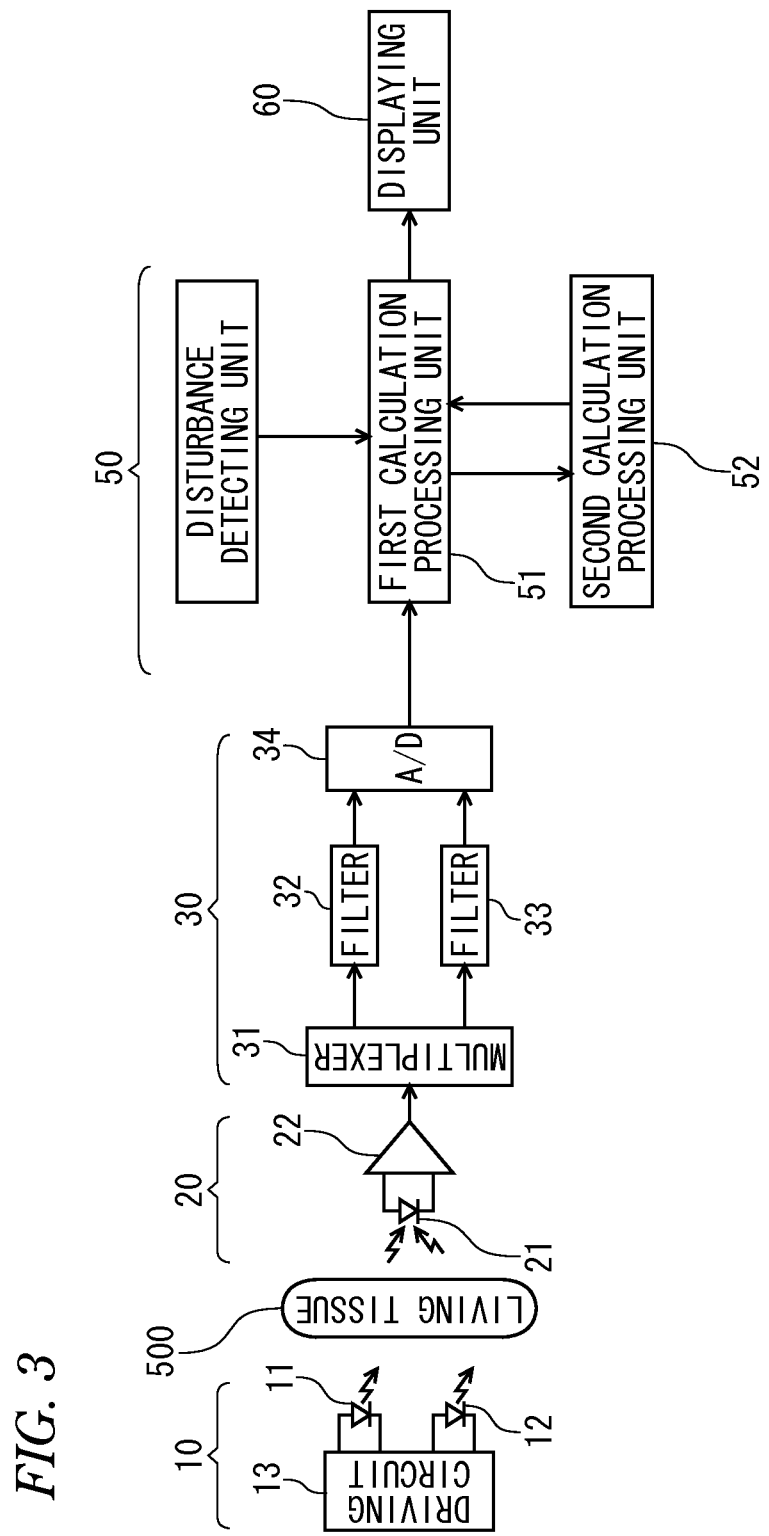
FIG. 3 is a view showing the functional configuration of a pulse oximeter 3 of a further example of the embodiment of the invention.

FIG. 3 is a view showing the functional configuration of a pulse oximeter 3 of a further example of the embodiment of the invention. Description of the components of the pulse oximeter 3 of the example which are similar to those of the pulse oximeter 1 that has been described with reference to FIG. 1 is omitted.

As shown in FIG. 3, the calculation processing unit 50 of the pulse oximeter 3 of the example includes the first calculation processing unit 51, the second calculation processing unit 52, and a disturbance detecting unit 54. The disturbance detecting unit 54 is connected to the first calculation processing unit 51. The disturbance detecting unit 54 may include various configurations for detecting a disturbance cause which generates noises in a result of a measurement that is performed on a biological signal by using the functions achieve by the pulse oximeter 3, such as the oxygen saturation of arterial blood, the pulse rate, and the like. Examples of such configurations are an acceleration sensor which detects a body motion, and an optical sensor which detects entering of extraneous light. In the case where the disturbance detecting unit 54 detects a disturbance cause such as a body motion or extraneous light, the unit notifies the first calculation processing unit 51 of the detection of the given disturbance noise, and the first calculation processing unit 51 which receives the notification determines that the given conditions are satisfied, and causes the second calculation processing unit 52 to execute the specific calculation process.

The logic circuit disposed in the second calculation processing unit 52 of the pulse oximeters 1, 2, 3 in the examples is not limited to the above-described three kinds of logic circuits. Particularly, it is preferable to dispose a logic circuit specialized for a process of a kind which is difficult to be handled by the first calculation processing unit 51. In the pulse oximeters 1, 2, 3 in the examples, an FPGA is used as the second calculation processing unit 52. In place of an FPGA, for example, a semi-custom LSI such as an ASIC (Application Specific Integration Circuit) may be used as the second calculation processing unit 52. A configuration which is specific to one of the pulse oximeters 1, 2, 3 in the examples may be provided to the pulse oximeter of another example.

In the above, the pulse oximeters have been described as the examples of the preferred embodiment of the biological signal measuring apparatus of the invention. However, the biological signal measuring apparatus is not limited to a pulse oximeter, and may be used in, for example, an electrocardiograph which can measure an electrocardiogram, or an electroencephalograph which can measure brain waves. In this case, the second calculation processing unit 52 may be configured so as to perform a process (for example, a process of analyzing arrhythmia in an electrocardiogram, or that of analyzing brain waves) which imposes a heavy load on the CPU, and which consumes large power.

The technical scope of the invention is not limited to the scope of the description of the embodiment. It is obvious to those skilled in the art that various modifications and improvements may be made to the embodiment.

According to the biological signal measuring apparatus of the invention, in the case where the first calculation processing unit satisfies the given conditions, the first calculation processing unit causes the second calculation processing unit to execute the calculation process, whereby the calculation amount of the first calculation processing unit can be reduced as compared with the case where the process is executed only by the first calculation processing unit. Therefore, for example, a CPU operating at a lower clock frequency can be used in the first calculation processing unit, so that the power consumption can be reduced. In a pulse oximeter which is driven by batteries, consequently, the life of the batteries can be prolonged. Even when a high-performance component (for example, a CPU) is not employed as the first calculation processing unit, and the component is replaced with a general-purpose component, moreover, it is possible to maintain the performance of the biological signal measuring apparatus, and hence it is possible to realize development in which components can be flexibly selected.

According to the biological signal measuring apparatus of the invention, the first and second calculation processing units can be controlled independently from each other, and high-load processes (a process of eliminating body motion noise and that of eliminating extraneous light noise) can be distributed. Therefore, power supplies can be ON/OFF-controlled as required, and hence the power consumption can be reduced.

According to the biological signal measuring apparatus of the invention, the first calculation processing unit performs the determination based on the predetermined conditions, or, if the load of the calculation process due to the noise component exceeds a predetermined level, performs an input to the second calculation processing unit. Therefore, the second calculation processing unit is activated only when required. Consequently, the power consumption can be reduced.

What is claimed is:
1. A biological signal measuring apparatus including:
   a biological signal measuring sensor configured to measure a biological signal;
   a first processor configured to perform a first processing on the measured biological signal, a second processor configured to perform a second processing on the measured biological signal, wherein the first processor and the second processor are independently controllable to execute the first processing and the second processing, and the first processor is further configured to determine at least one of the measured biological signal satisfies a given condition and a load of the first processor performing the first processing exceeds a given level, and control the second processor to perform the second processing based on a result of the determination.

2. The biological signal measuring apparatus according to claim 1, wherein a processing efficiency of the second processor performing the second processing is higher than a processing efficiency of the first processor performing the second processing.

3. The biological signal measuring apparatus according to claim 1, wherein the second processing comprises at least one of a simple process, a routine process, and a parallel process.

4. The biological signal measuring apparatus according to claim 1, wherein the second processing is a calculation process specialized for elimination of at least one of body motion noise and extraneous light noise in the measured biological signal.

5. The biological signal measuring apparatus according to claim 1, wherein the given condition comprises at least one of reduction of a quality of the measured biological signal, detection of a body motion, and detection of extraneous light.

6. The biological signal measuring apparatus according to claim 1, wherein, in the second processor, a unit data length for the second processing is shorter than a unit data length for the first processing performed by the first processor.

7. The biological signal measuring apparatus according to claim 1, wherein the first processor is further configured to supply a result of the first processing to the second processor.

8. The biological signal measuring apparatus according to claim 7, wherein, in a case where the load of the first processor performing the first process exceeds the given level, the first processor is further configured to supply a result of the first processing to the second processor.

9. The biological signal measuring apparatus according to claim 1, wherein the first processor further comprises:

a disturbance detector configured to detect a disturbance cause of noises in a result of measurement of the biological signal, and wherein in a case where the disturbance detector detects the disturbance cause, the first processor is further configured to control the second processor to perform the second processing.

10. The biological signal measuring apparatus according to claim 9, wherein the disturbance detector comprises at least one of an acceleration sensor configured to detect a body motion and an optical sensor configured to detect extraneous light.

11. The biological signal measuring apparatus according to claim 1, wherein the first processor is further configured to determine an optimum result of the first processing and the second processing and output the optimum result to a display.

12. The biological signal measuring apparatus according to claim 1, wherein the biological signal measuring sensor comprises:

a light emitter configured to illuminate living tissue containing arterial blood flow, with light beams of two different wavelengths at different timings; and a light receiver configured to receive the light beams that are emitted from the light emitter and transmitted through or reflected from the living tissue, and configured to convert the light beams to an electric signal corresponding to intensities of the received light beams of the respective wavelengths, and wherein the first processor is further configured to calculate a ratio of pulsation components of an absorbance due to the arterial blood flow with respect to the light beams of two wavelengths, from data which are produced based on the electric signal, and calculate an oxygen saturation of arterial blood based on the ratio of pulsation components.

13. The biological signal measuring apparatus according to claim 12, wherein the light beams of two different wavelengths include a red light beam and an infrared light beam.

14. The biological signal measuring apparatus according to claim 1, wherein the second processor comprises a field programmable gate array (FPGA).

15. A pulse oximeter comprising:

a biological signal measuring sensor configured to measure a biological signal;

a first processor configured to calculate oxygen saturation of arterial blood from the measured biological signal, a second processor configured to remove noise from the measured biological signal, wherein the first processor and the second processor are independently controllable to calculate the oxygen saturation of arterial blood and remove noise from the measured biological signal, and the first processor is further configured to determine that noise exists in the measured biological signal and a load of the first processor calculating the oxygen saturation of arterial blood, control the second processor to remove the noise from the measured biological signal based on a result of the determination that noise exists in the measured biological signal and that the load of the first processor exceeds a threshold load level, and calculate the oxygen saturation of arterial blood based on the measured biological signal from which the noise is removed by the second processor.

16. A biological signal measuring apparatus including:

a biological signal measuring sensor configured to measure a biological signal;

a first processor configured to analyze the measured biological signal, a second processor configured to remove noise from the measured biological signal, wherein the first processor and the second processor are independently controllable to execute the first processing and the second processing, and the first processor is further configured to determine that the measured biological signal includes noise and that a load of the first processor analyzing the measured biological signal exceeds a given level, and control the second processor to remove the noise from the measured biological signal based on a result of the determination.

* * * * *